United States Patent [19]

Schuster

[11] 4,380,485

[45] Apr. 19, 1983

[54] METHOD OF MAKING BREATHABLE RECEPTACLES

[76] Inventor: Samuel J. Schuster, 617 Vallombrosa, Pasadena, Calif. 91107

[21] Appl. No.: 196,824

[22] Filed: Oct. 14, 1980

Related U.S. Application Data

[60] Continuation-in-part of Ser. No. 55,160, Jul. 6, 1979, abandoned, which is a division of Ser. No. 955,221, Oct. 27, 1978, abandoned.

[51] Int. Cl.$^3$ ................... B32B 31/00; B32B 3/00; B26F 15/28
[52] U.S. Cl. ................................ 156/254; 156/271; 156/344; 428/60; 225/2; 229/DIG. 14
[58] Field of Search ............... 156/217, 290, 271, 247, 156/254, 308.4, 344; 206/497, 439, 438, 440, 484.1; 229/53, DIG. 14, 55; 493/498, 470, 199, 200, 209, 341; 225/2, 4; 428/60, 198, 33, 103, 137, 133

[56] References Cited

U.S. PATENT DOCUMENTS

| | | | |
|---|---|---|---|
| 2,351,498 | 6/1944 | Fowler | 156/254 |
| 2,847,086 | 8/1958 | Müller | 428/133 |
| 3,207,643 | 9/1965 | Sorg | 156/254 |
| 4,097,383 | 6/1978 | Ohtani et al. | 156/254 |

Primary Examiner—Edward C. Kimlin
Assistant Examiner—Louis Falasco
Attorney, Agent, or Firm—Fraser and Bogucki

[57] ABSTRACT

Disposable receptacles for storing articles in sterile condition and having breather means integral with the walls thereof, as well as apparatus and methods for making such receptacles and the materials therefor, are disclosed. The receptacles are fabricated of a laminate comprising a layer of breathable barrier material such as paper and a layer of thermoplastic, polymeric material such as polyethylene.

The breather means may be made by heat sealing the thermoplastic layers of a pair of laminated sheets together at small, selected areas and then separating the sheets causing localized delamination of the layers and the formation of ruptured, blister-like projections in the thermoplastic layers at the heat seal positions.

6 Claims, 12 Drawing Figures

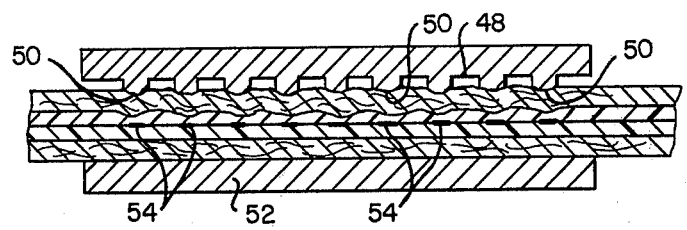
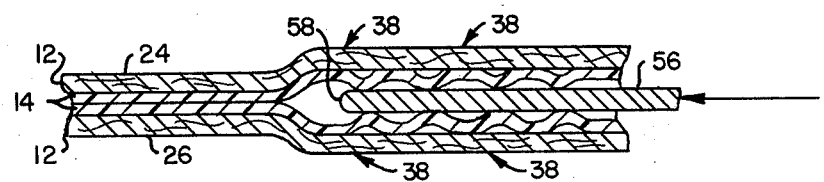
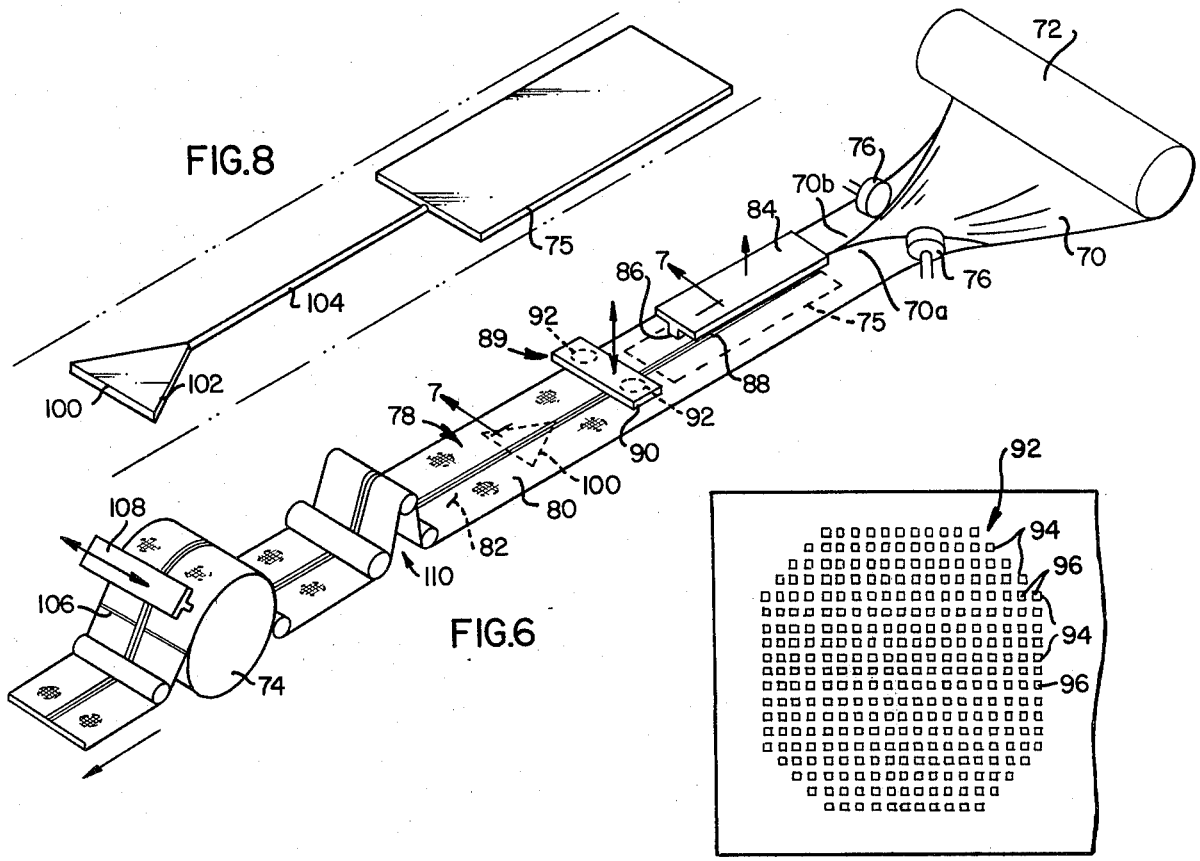
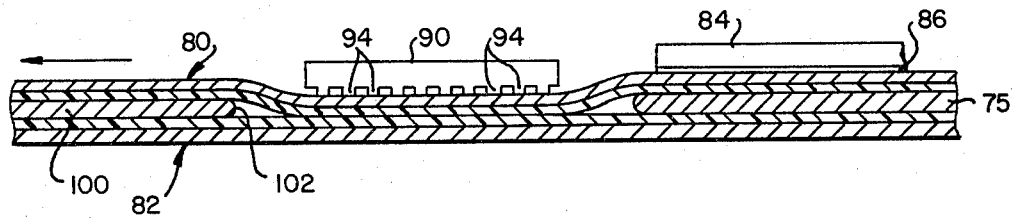

METHOD OF MAKING BREATHABLE RECEPTACLES

RELATED APPLICATIONS

This application is a continuation-in-part of abandoned application Ser. No. 55,160 filed July 6, 1979 and entitled "Method of Making Breathable Receptacles", which application was a division of abandoned application Ser. No. 955,221 filed Oct. 27, 1978 and entitled "Sterilizable Receptacles And Methods And Apparatus Relating Thereto".

BACKGROUND OF THE INVENTION

1. Field of the Invention

This invention relates to a method of manufacturing disposable, breathable receptacles for storing articles in sterile condition.

2. Description of the Prior Art

Currently, receptacles for sterile packaging of articles, and primarily those used for medical applications, fall principally within three general categories: pouches with one side made of polyethylene-coated paper or of polyethylene film and the other side consisting of a breathable material such as paper or "Tyvek" (a spun polyolefin of the du Pont Company); pouches or bags having an all-paper construction utilizing adhesive bonds with the entire surface area of the receptacle serving as the breathing membrane; and pouches or bags with walls made substantially entirely of a material, typically polyethylene or polypropylene, which is impermeable to both microorganisms and sterilizing vapor and having a breathable strip or patch covering a slit or port in the wall.

Receptacles in current use often have limited shelf lives due to deterioration of the membrane material as a result of changes in ambient temperature and humidity which cause flexing, distortion and sometimes pinholding of the membrane material. This is particularly true of receptacles whose breathing membrane constitutes a large portion of the overall area of the receptacle such as those in which the membrane forms an entire wall, or both walls, of the receptacle. Stresses applied to the membrane walls of such receptacles can be transferred to a vulnerable spot accelerating the formation of pinholes or otherwise weakening the structure sufficiently to eventually create a break through which microorganisms can enter. Another disadvantage of such receptacles is that the stored article is directly exposed to large areas of the fibrous membrane with the possibility of dislodging fibers through abrasion or other physical contact.

Moreover, receptacles that are fabricated of two materials are expensive. The breathable membrane, if paper, must be surgical grade and is significantly more expensive than ordinary paper while "Tyvek" is several times the price of paper membrane material. Some such receptacles have small windows or ports covered by a patch of vapor-permeable material. The manufacture of such receptacles requires exact registration between the port, patch and the mechanism that seals the patch to the receptacle thereby necessitating the use of additional apparatus which substantially increases the cost of the final product.

SUMMARY OF THE INVENTION

Receptacles made in accordance with the present invention solve the above-described problems by utilizing readily available, low cost pre-laminated material such as polyethylene-coated paper. In accordance with one specific form of the receptacle, there is provided a pair of opposed walls joined about a portion of their peripheries. At least one of the walls is a laminate including an outer layer of a material such as paper which is impermeable to microorganisms but highly permeable to sterilizing vapor, and an inner layer of a polymeric material such as polyethylene. At least a portion of the laminated wall has breathers for the introduction and removal of sterilizing vapor, the breathers comprising ruptured portions of the inner layer. The ruptures in the delaminated portion of the inner layer at each breather position are substantially smaller in area than the corresponding delaminated portion of the outer layer. Such a receptacle is exceptionally strong because of the reinforcing provided by the layer of polymeric material. The stored product is in contact only with that layer and hence completely protected by it. The area of individual ruptures is so small that virtually no paper is exposed and contact between the paper and the product is thereby effectively precluded.

By incorporating the breathing area directly into the wall of the receptacle, that is, by making the breathing area an integral part of the wall structure, dual material construction such as required in some prior art receptacles is eliminated. The speed of manufacture may therefore be increased since heat sealable layers are bonded to each other through the paper substrate allowing an increase in sealer temperatures (which are not critical) with a concomitant decrease in dwell time. Moreover, the relatively small size of the ruptures in the inner layer provides an additional barrier to any microorganisms that might penetrate the breathing areas of the outer layer. Sterilizing vapor, however, easily passes through the small ruptures.

In accordance with the invention, the fabrication of the receptacles, or of breathable laminate usable for such receptacles, is carried out in a unique and highly efficient manner which takes advantage of the fact that the strength of a heat seal bond between the thermoplastic layers of confronting or superimposed sheets of laminate is initially greater than the delamination resistance of the laminate. Generally, in accordance with one example of the method, the walls are heat sealed together at small, selected areas and then separated causing localized delamination of the layers and the formation of ruptured, blisterlike projections in the thermoplastic layer of one or both walls at the location of each of the small heat seals. Only a relatively small number of these ruptures are necessary to provide adequate breathing to facilitate the sterilization of the contents of the final package by a vapor sterilization process.

DESCRIPTION OF THE DRAWINGS

The present invention will be more fully understood from the detailed description of the preferred embodiment, below, taken in conjunction with the accompanying drawings in which:

FIGS. 4 and 5 are side elevation views, in section, of portions of laminates and apparatus to illustrate certain of the steps in the fabrication of receptacles such as shown in FIGS. 1-3;

FIG. 6 is a somewhat schematic, perspective view of an apparatus for making receptacles of the type shown in FIGS. 1-3;

FIG. 7 is a side elevation view, partly in crosssection, of a portion of the apparatus of FIG. 6 as seen along 7—7;

FIG. 8 is a perspective view showing the details of certain of the elements of the apparatus of FIG. 6;

FIG. 9 is a bottom view of a portion of one of the heat sealers utilized in the apparatus of FIG. 6;

DETAILED DESCRIPTION OF THE PREFERRED EMBODIMENT

At the outset, it is to be noted that in the accompanying drawings the thicknesses of the laminates and layers comprising the laminates have all been greatly exaggerated in order to clearly show their interrelationships. Further, certain of the views are somewhat schematic or idealized in order to facilitate description of the invention and to avoid confusion. It will also be evident that a great many combinations of materials (both opaque and transparent), overall package dimensions, material properties, specific package configurations, and so forth, fall within the purview of the claimed invention. Only relatively few specific examples are shown and discussed herein and these should not be construed as exhaustive.

The term "sterilizing vapor" used herein is intended to include vapors such as ethylene oxide, steam, or the like, that are passed into the interior of a sealed package through a breathable membrane or the like and withdrawn, typically under partial vacuum, to effect sterilization of the contents of the package.

Figure 1:
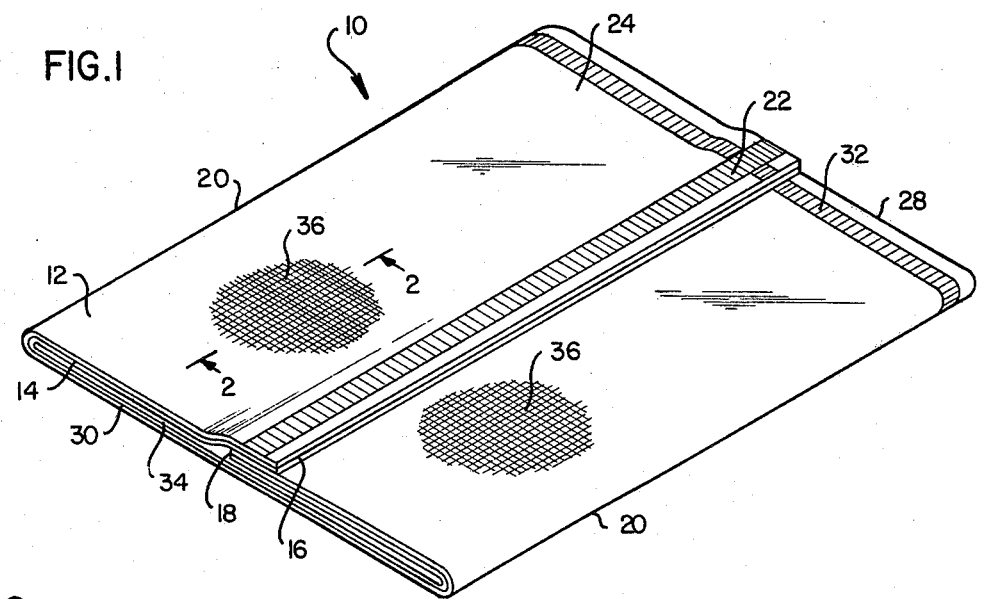
FIG. 1 is a perspective view of a sterilizable receptacle made in accordance with the invention.
Figure 2:
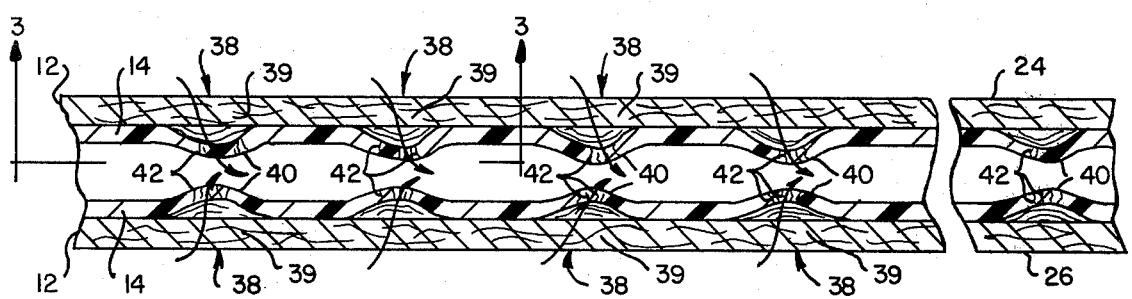
FIG. 2 is an enlarged cross-section view of a portion of the receptacle of FIG. 1 as seen along 2—2.
Figure 3:
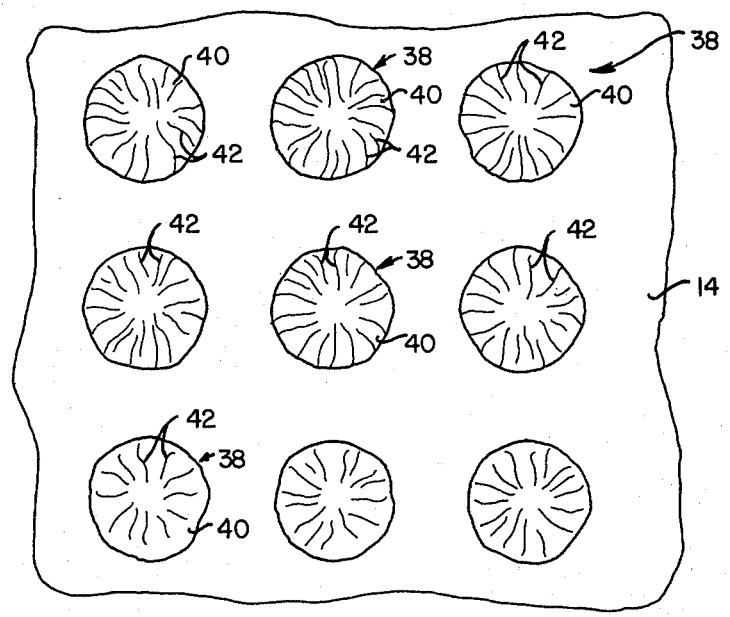
FIG. 3 shows a portion of the inner layer of the laminated wall of the receptacle as seen along 3—3 in FIG. 2.

FIGS. 1-3 show a disposable, breathable receptacle for receiving articles to be stored in sterile condition. The receptacle takes the form of a bag 10 made from a heat sealable, pre-laminated sheet or stock comprising an outer layer 12 of paper, "Tyvek", or the like, and a thermoplastic, polymeric film forming an inner layer 14 bonded to the outer layer 12. The layer 12 is highly permeable to sterilizing vapor but impermeable to microorganisms so as to define, in the final package, an effective barrier to the entry of contaminating agents. By way of specific example, the laminate can be polyethylene-coated Kraft paper which is commonly available at exceedingly low cost and which provides a strong, protective envelope for the article(s) to be stored.

The laminated sheet has longitudinal edge margins 16 and 18 and is folded along parallel, longitudinal fold lines 20 so as to bring the margins 16 and 18 into overlapping relationship. These margins are joined along the entire length of the bag by a longitudinal heat seal 22 thereby forming the laminated sheet into a flat tubular structure having opposed faces or walls 24 and 26. Transverse edges 28 and 30 define the ends of the bag. One of the ends is sealed by a transverse heat seal 32 while the other end has an opening 34 for receiving the article(s) to be stored.

It will be evident to those skilled in the art that in the alternative, separate, laminated sheets may be superimposed to define the walls 24 and 26 and joined by heat sealing or other bonding along their peripheries save for an opening for inserting the article to be packaged. Such a construction is known in the art as a pouch and constitutes another form that the receptacle of the present invention may take.

In the specific embodiment of the receptacle depicted in FIGS. 1-3, the laminated wall has two arrays 36 of small breathers 38 formed by a method which will be presently described. The breathers 38 allow sterilizing vapor to be introduced into and withdrawn from the interior of the final, sealed package to effect sterilization of the contents in accordance with well known techniques.

As shown in FIG. 1, the arrays 36 are generally circular with one array on each side of the longitudinal center line of the bag 10, but it will be obvious that virtually any configuration can be used and that breathers can be distributed across the entire area of one wall or both walls. It is advantageous, however, to confine the breathers to relatively small regions of the bag wall so as not to adversely affect the strength of the bag and to avoid any possible contact between the enclosed article and the layer 12 which, as stated, is typically a fibrous material such as paper.

The breathers 38 are defined by discrete portions of the wall where the outer and inner layers 12 and 14, respectively, are delaminated or separated. Each delaminated portion 39 of the outer layer 12 comprises an individual breathing area in the outer layer. Each delaminated portion 40 of the inner layer 14 includes vapor-permeable ruptures 42 substantially smaller in area than the corresponding breathing area 39 in the outer layer. The relatively small size of the ruptures 42 provides an additional barrier to any microorganisms that might penetrate the breathing areas 39 of the outer layer.

Contact between the enclosed article and the layer 12 is avoided by virtue of the small size of the ruptures 42. In the particular form of the receptacle under consideration, further protection against contact between the contents of the package and the paper layer is afforded by positioning the arrays 36 away from the central portion of the bag within which portion the article tends to settle during storage. For example, the arrays 36 in the embodiment of FIG. 1 are located adjacent the opening 34.

Turning now also to FIGS. 4 and 5, a method of making the breathers 38 in accordance with the invention will now be described. Although the description is in the context of a bag such as that shown in FIGS. 1-3, the method will be applicable generally to other receptacle constructions and to the production of breathable laminates per se from laminated stock for use in medical packaging or the like. Following the formation of the laminated sheet into a tubular structure by the application of the longitudinal heat seal 22 to join the margins, a heat sealer 48 having, for example, a circular working surface consisting of a gridwork of individual, square faces 50, is applied to the outer, paper layer 12 of one of the walls 24. In accordance with one practical example of the invention, the heat seal faces 50 of the heat sealer 48 are 1/16" squares with 1/16" spacings between rows and columns of seal faces. A backing plate 52 positioned opposite the heat sealer 48 supports the bag during this sealing operation. The heat sealer 48 effects a series of individual seals 54 between the confronting thermoplastic layers of the walls 24 and 26. The impressions made by the heat sealer 48 remain on the outside surface of the paper as shown in FIG. 1.

Following this operation and preferably while the individual seals are still at somewhat elevated temperature, a separator plate 56 having a tapered or rounded leading edge 58 is inserted into the tubular bag structure to separate the walls 24 and 26. By performing this step while the seals are still hot, the bond between the outer and inner layers 12 and 14 is slightly weakened and helps prevent fibers from being dislodged from the outer layer 12. Since at the outset the strength of the individual heat seals is greater than the delamination resistance of the laminate, a small portion of the polymeric layer under and about each seal is pulled away from the paper as the separator plate advances resulting in localized delamination of the inner and outer layers. Further advancement of the plate 56 apparently causes the portions of the inner layer about the individual seals to stretch and rupture resulting in a structural configuration appearing somewhat like that shown in FIG. 3. It will be understood that FIG. 3 is highly idealized; in practice, when viewed under magnification, the shapes of the blister-like, ruptured projections appear quite irregular.

The resulting bag is strong, provides excellent protection and incorporates, in an exceedingly simple and low cost manner, an integral breather.

FIGS. 6-9 show in somewhat schematic form an apparatus for making the bags of FIGS. 1-3 on a commercial scale. Following manufacture of the bag on the apparatus of FIGS. 6-9, an article is inserted and the open end sealed with a transverse heat seal. As is well known in the art, the bag may be formed, filled and sealed on a single machine combining these operations. In either case, the resulting package is then exposed to a sterilizing vapor which permeates through the breathers and sterilizes the article and the interior surfaces of the package. After purging of the sterilizing vapor, the package is stored until the enclosed article is ready for use. Opening of the bag can be facilitated in any of a number of ways well known in the art.

The bags are formed from a continuous web 70 of the earlier described laminated stock drawn from a supply roll 72 and maintained under the required tension. The web 70 is advanced step-by-step a distance of one bag length by an intermittently rotatable feed drum 74 actuated by a suitable drive unit (not shown). As it advances, the web 70 is folded in well known fashion about a plate mandrel 75 by the action of forming and folding members collectively represented by the angularly oriented roller elements 76. The web 70 is thus formed into a continuous sleeve or tube 78 with the margins 70a and 70b being disposed in overlapping relation. The tube 78 thus envelopes the plate mandrel 75 which is interposed between an upper wall 80 and a lower wall 82 of the flattened tube 78.

During each dwell between successive advancements of the tube 78, a longitudinal, vertically movable heat sealer 84 disposed above the plate mandrel 75 and having a single, central heat seal bar 86 is operated to join the confronting margins of the web 70 by means of a heat seal 88.

Following application of the longitudinal heat seal 88, small individual heat seals joining the heat sealable layers of the walls 80 and 82 are formed at a heat seal station 89 just downstream of the longitudinal heat sealer 84. The seals are applied by a heat sealer 90 having a pair of spaced, circular sealer members 92 each consisting of an array of projecting sealing elements 94 arranged in a grid pattern. Each sealing element 94 has a square face 96 approximately 1/16" on a side and spaced apart a distance of 1/16" both longitudinally and transversely as already described. Again, the size, shape and spacing of the sealing elements 94 and their faces 96 as well as the overall configuration, size and placement of the breather arrays are not limited to that described which is to be construed as exemplary only.

The sealer members 92, one of which is disposed on one side of the longitudinal center line of the tube 78 and the other of which is located on the other side of the tube center line, join the superimposed walls of the tube 78 with arrays of individual heat seals as already described in connection with FIGS. 1-5.

Disposed inside the tube 78 just downstream of the sealing station 89 is a V-shaped plate 100 the function of which is to separate the walls 80 and 82 to produce an array of breathers in the manner described above in connection with FIGS. 4 and 5. The separator plate 100, which has a rounded or gradually tapered leading edge 102, is held in place against the movement of the advancing tube by a rod or wire 104 connecting the tip of the plate 100 with the center of the trailing edge of the plate mandrel 75 (FIG. 8). The separator plate 100 may assume shapes other than that specifically shown and alternative means will suggest themselves to those skilled in the art for separating the portions of the walls 80 and 82 that have been sealed by the heat sealer 89. For example, the walls can also be separated by a surge of pressurized air introduced into the tube via a conduit using a mechanism, for example, generally along the lines as disclosed in U.S. Pat. No. 3,837,972.

Following separation of the walls 80 and 82 by the plate 100, the tube is drawn about the feed drum 74. At this station along the path of the tube a transverse seal 106 joining the walls of the tube is applied by a transverse heat sealer 108 which is pressed down on the tube during each dwell period. The position of the transverse seal 106 relative to the breather arrays is controlled by a three-roller compensator mechanism 110 the operation and structure of which is well known in the art. From the feed drum 74 the tube is advanced to a cutting station (not shown) where the tube is separated into individual bags. It will be appreciated that bag fabrication as well as filling and sealing of the resulting package may be performed on a single "form and fill" machine.

Figure 10:
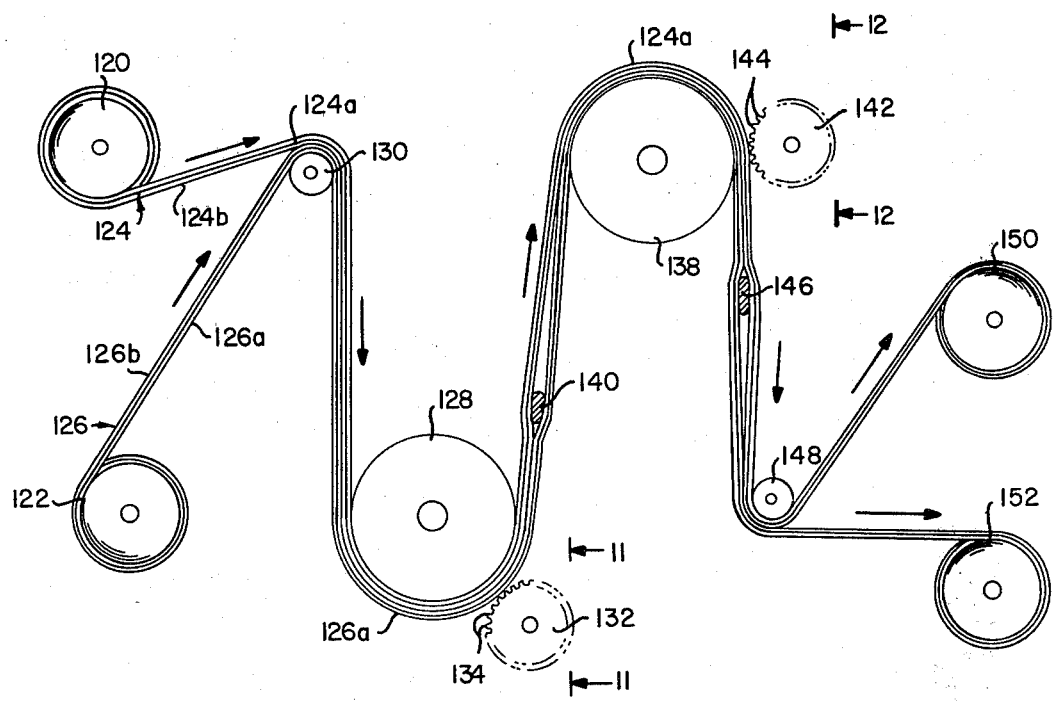
FIG. 10 shows, in somewhat schematic form, a side elevation view of an apparatus for making a breathable laminate.

FIG. 10 shows an apparatus for the continuous, high speed fabrication of webs of breathable laminate for use in making sterilizable receptacles of the type already discussed as well as breathable, removable covers for trays such as that disclosed in U.S. Pat. No. 4,022,324. Such breathable laminate may also be employed for making vapor-permeable, peelable strip material for medical packages such as disclosed in U.S. Pat. No. 3,472,369.

The apparatus of FIG. 10 includes a pair of supply rolls 120 and 122 for supplying webs 124 and 126 each of which is a laminated structure of paper 124a, 126a and heat sealable material 124b, 126b, or the equivalent as already described. The webs 124 and 126 are drawn off the rolls 120 and 122 by a first drive roller 128. The webs converge and their heat sealable layers 124b and 126b are brought into contact about an idler roller 130 disposed between the supply rolls and the drive roller 128.

A first rotary heat sealer 132 adjacent the drive roller 128 and biased into contact with the paper layer 126a applies a first set of small, individual heat seals bonding the heat sealable layers 124b and 126b. The first rotary heat sealer 132, which has a plurality of projecting heat seal elements 134, may extend across the entire width of the webs. Alternatively, the length of the heat sealer 132 and its position along the width of the webs may be chosen so as to apply the small, individual heat seals along any selected path along the length of the webs. For example, as shown in FIG. 11, the roller 132 may have a length somewhat less than one-half the overall width of the superimposed webs 124, 126 and be positioned to one side of the center line 136 of the webs.

Figure 11:
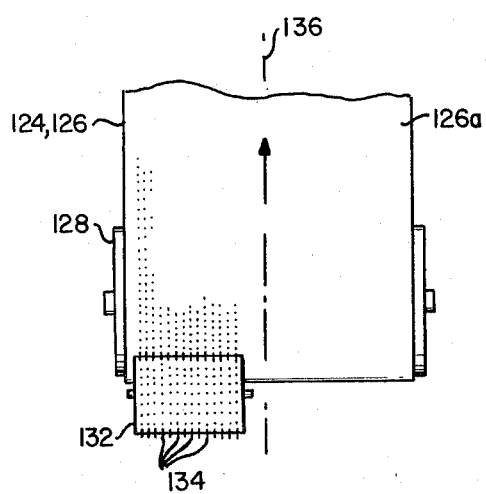
FIGS. 11 and 12 are end elevation views of portions of the apparatus of FIG. 10 as seen along 11—11 and 12—12 in FIG. 10.

In the example of FIG. 11, the heat seal elements 134 projecting from the rotary heat sealer 132 are arranged in parallel rows to provide a grid-like pattern of individual seals similar to the pattern previously described. Alternatively, the elements 134 can be grouped in virtually any desired formation.

The webs 124 and 126 are drawn off the first drive roller 128 by a second drive roller 138 about which the heat sealable layers of the webs are again brought into intimate contact. Positioned between the first and second drive rollers 128 and 138 is a stationary separator plate 140 of metal or plastic, such as "Teflon", inserted between the webs 124 and 126 for separating the webs in the manner already described with the result that discrete breathers are produced in heat seal layers 124b and 126b at the positions of the heat seals formed by the rotary sealer 132. Preferably, the distance along the web between the heat sealer 132 and the plate 140 is sufficiently short so that the heat seals made by the sealer 132 are still at elevated temperature when they arrive at the leading edge of the plate 140.

Figure 12:
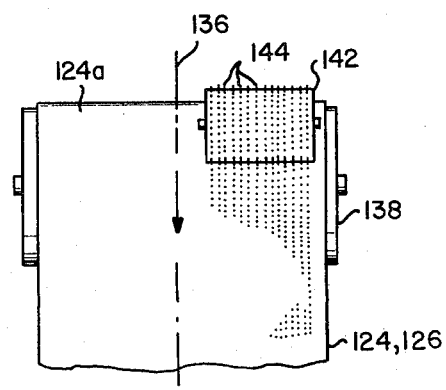

The second drive roller 138 has coacting therewith a second rotary heat sealer 142 which applies a second set of small, individual heat seals through the paper layer 124a and which may be identical to the first heat sealer 132. Thus, the sealer 142 may extend across the entire width of the webs or only across a portion of the width as shown in the example of FIG. 12. In the event the paths of the heat seals produced by the rotary sealers 132 and 142 overlap (such as would be the case, for example, if they extended the entire width of the webs), the drive units of the sealers 132 and 142, which drive units have been omitted from the drawing for the sake of clarity, should be synchronized so that the second set of seals are staggered, that is, out of registration, with respect to the first set of seals. As in the case of the first sealer 132, the individual sealing elements 144 of the second sealer may be arranged in virtually any pattern.

Downstream of the second roller 138 is a second, stationary separator plate 146 whose function and structure is the same as the first plate 140. The webs proceed about an idler roller 148 and from there they are separately wound into rolls 150 and 152. The breathable webs thus produced are ready to be used in the manufacture of bags, pouches, tray lids, or the like, or other products which may employ such laminates. Instead of being wound into supply rolls 150, 152, the webs may proceed directly to bag or pouch-making mchines or to "form and fill" packaging machines.

Although there have been described a number of alternative forms and modifications of the various aspects of the invention, it will be appreciated that the invention encompasses all modifications and variations falling within the scope of the appended claims.

What is claimed is:

1. A method of making a breathable receptacle for storing an article in sterile condition, the receptacle being constructed of a laminate comprising a layer of paper or the like impermeable to microorganisms but highly permeable to sterilizing vapor and a layer of thermpolastic, polymeric material, the strength of a heat seal bond between layers of the polymeric material being initially greater than the delamination resistance of the laminate, the method including the steps of:
   superimposing first and second sheets of said laminate with the polymeric layers in confronting relation;
   heat sealing the polymeric layers of said sheets together at a plurality of small areas;
   separating the sheets thereby rupturing the polymeric layer of at least one of the sheets at the positions of the small areas; and
   joining the sheets together to define the receptacle.

2. A method of making a breathable bag for storing an article in sterile condition, the bag being constructed from a laminated web having longitudinal edge margins and comprising a layer of paper or the like impermeable to microorganisms but highly permeable to sterilizing vapor and a layer of thermoplastic, polymeric material, the strength of a heat seal bond between layers of the polymeric material being initially greater than the delamination resistance of the web, the method including the steps of:
   folding the web along longitudinal fold lines to bring the longitudinal edge margins of the web into overlapping relationship;
   heat sealing the overlapping edge margins together with a continuous, longitudinal heat seal to form a flattened tube having confronting walls, the layer of paper, or the like, constituting the outer layer of the tube;
   heat sealing together the polymeric layers of the confronting walls at a plurality of small areas;
   separating the walls thereby rupturing the polymeric layer of at least one of the walls at the positions of the small, heat sealed areas; and
   applying a transverse heat seal across the width of the flattened tube to form a sealed bag end.

3. A method of making a breathable laminate from laminated stock including a layer of paper or the like and a layer of heat sealable material, said method comprising the steps of:
   bringing the heat sealable layer of a sheet of said stock into contact with a heat sealable surface;
   bonding said heat sealable layer of said sheet to said heat sealable surface with a plurality of small, individual heat seals applied through said paper layer, the strength of said bonds being initially greater than the delamination resistance of said layers; and
   separating said sheet from said heat sealable surface thereby rupturing the heat sealable layer at the locations of the various individual heat seals.

4. A method of making a breathable laminate from laminated stock comprising a layer of paper or the like and a layer of heat sealable material, the strength of a heat seal bond joining layers of said heat sealable material being initially greater than the delamination resistance of the laminate, said method comprising the steps of:

superimposing first and second sheets of said stock with the layers of heat sealable material in contact;

bonding the heat sealable layers to each other with a plurality of small, individual heat seals applied through the paper layer of at least one of the sheets; and separating the sheets thereby rupturing the heat sealable layer of at least one of the sheets at the positions of the individual heat seals.

5. A method of continuously making a breathable laminate from laminated stock comprising a layer of paper or the like and a layer of heat sealable material, said method comprising the steps of:

superimposing first and second, continuous webs of said stock with the layers of heat sealable material of said webs in contact;

bonding the heat sealable layers to each other with a first set of small, individual heat seals applied through the paper layer of the first web;

separating the webs thereby rupturing the heat sealable layer of at least one of the webs at the positions of the individual heat seals of the first set of seals;

again superimposing said webs, bringing the layers of heat sealable material of said webs into contact;

bonding the heat sealable layers to each other with a second set of small, individual heat seals applied through the paper layer of the second web, said second set of heat seals being staggered with respect to the first set of heat seals; and separating the webs thereby rupturing the heat sealable layer of at least one of the webs at the positions of the individual heat seals of the second set of seals.

6. A method of continuously making a breathable laminate from laminated stock comprising a layer of paper and a layer of heat sealable material, the strength of a heat seal bond joining layers of said heat sealable material being initially greater than the delamination resistance of the laminate, said method comprising the steps of:

superimposing first and second, continuous webs of said stock with the layers of heat sealable material of said webs in contact and the edges of said webs in registration, said superimposed webs having a common, longitudinal center line;

bonding the heat sealable layers to each other with a first set of small, individual heat seals applied through the paper layer of the first web along a path on one side of the center line;

separating the webs thereby rupturing the heat sealable layer of at least one of the webs at the positions of the individual heat seals of the first set of seals;

again superimposing said webs, bringing the layers of heat sealable material of said webs into contact;

bonding the heat sealable layers to each other with a second set of small, individual heat seals applied through the paper layer of the second web along a path on the other side of the center line; and separating the webs thereby rupturing the heat sealable layer of at least one of the webs at the positions of the individual heat seals of the second set of seals.

* * * * *